United States Patent [19]

Pilley

[11] 4,385,064
[45] May 24, 1983

[54] METHOD FOR TREATING SICKLE CELL ANEMIA

[75] Inventor: Gerard A. Pilley, Sceaux, France

[73] Assignee: Laboratories Innothera, S.A., Arcueil, France

[21] Appl. No.: 244,286

[22] Filed: Mar. 16, 1981

Related U.S. Application Data

[63] Continuation of Ser. No. 878,601, Feb. 16, 1978, abandoned.

[51] Int. Cl.³ ............................................. A61K 31/38
[52] U.S. Cl. .................................................... 424/275
[58] Field of Search ......................................... 424/275

[56] References Cited

U.S. PATENT DOCUMENTS 4,005,095 1/1977 Robba et al. ........................ 424/275

OTHER PUBLICATIONS

*The Merck Index*, Ninth Ed., (1976), Merck & Co., Inc., Rahway, N.J., p. 253.
*Science*, vol. 211, 30 Jan. 1981, pp. 468–470.
"Medical Diagnosis Treatment 1977", pp. 289–291.
*Arch Intern Med.*, pp. 698–705.
"Cetiedil: Its Potential Usefulness in Sickle Cell Disease", *Blood*, pp. 265–270.

*Primary Examiner*—Frederick E. Waddell
*Attorney, Agent, or Firm*—Cooper, Dunham, Clark, Griffin & Moran

[57] ABSTRACT

A method for the treatment of the acute pain crises of sickle cell anemia has been found which comprises the administration of the citrate or the oxalate salt of the 2-hexahydro-1H-azepin-1-yl)ethyl ester of α-cyclohexyl-3-thiopheneacetic acid.

4 Claims, No Drawings

METHOD FOR TREATING SICKLE CELL ANEMIA

This is a continuation of application Ser. No. 878,601 filed Feb. 16, 1978, now abandoned.

BACKGROUND OF THE INVENTION

Sickle cell anemia is a disorder in which the hemoglobin of the blood is primarily hemoglobin S. Hemoglobin S differs from normal hemoglobin in that valine is substituted for the normal glutamic acid in the 6-position of the $\beta$-polypeptide chains of hemoglobin. As a result of this structural difference, the reduced hemoglobin S molecules then tend to stack into filaments which further aggregate into the elongated sickled cell.

Spontaneous sickling of such red cells occur when the concentration is sufficiently high but it is further facilitated by anoxia, acidosis, hyperthemia or excessive chilling. Thus, factors such as fever, an infection, or exposure to cold contribute to the formation of reduced hemoglobin S thus increasing the concentration of this material with a resultant increase in sickling. The sickling process is generally reversible although it does eventually reach a point at which it is irreversible. When the irreversible stage is passed, the cells involved are removed from the circulation resulting in a deficiency of such cells in the circulation and chronic hemolytic anemia. As a consequence, the ordinary symptoms associated with anemia would be observed. In addition, the cells formed deposit on the walls of the blood vessels and this would then impede circulation in the blood vessels and bring about painful vaso-occlusive crises. An increase in blood viscosity also occurs.

Previous treatments of sickle cell anemia have been purely symptomatic involving the administration of sedatives to alleviate the pain or, when a prolonged severe painful crisis is involved, by the administration of multiple packed cell transfusion which serves to reduce the proportion of circulating sickling prone red cells below a level that can be induced to sickle.

As the mechanism of the sickling disorder has become known, various drugs have been investigated in an attempt to find a satisfactory one that would be effective against sickling. Sodium cyanate has produced improvements but it has been considered difficult and dangerous to use because it produces neuropathies. Urea was discarded after a double-blind study. It was found to be no more or less effective than hydration alone. Steroid hromones can be used but only in adults. Other materials that have been investigated are dimethyl adipimate, ergot alkaloids and vincamines but the effectiveness of these materials is still unclear.

SUMMARY OF THE INVENTION

It has now been found that certain salts of the 2-(hexahydro-1H-azepin-1-yl)ethyl ester of α-cyclohexyl-3-thiopheneacetic acid are useful for the treatment of sickle cell anemia. Specifically, the citrate and the oxalate salts are useful for this purpose and the monohydrate form of the citrate salt, which is known as Cetiedil, is particularly useful. More particularly, these compounds are useful for the treatment of the acute pain crises which occur in sickle cell anemia. When the compounds are administered to patients in such crises, there is very rapid relief of the severe pain of the crisis and a sensation of well-being is reported. Additional time or repeated administrations may be necessary for complete relief of the pain. In addition, although there may be some variation in results observed depending on the nature (location) of the pain involved in the crisis, some measure of relief has been observed in almost all cases.

The indicated effect of Cetiedil and the related compounds may be the result of one or more of the following factors but the invention should not be considered as limited by whether or not the indicated factors are, in fact, responsible for the effect. Thus, Cetiedil is not a general sedative but it is a peripheral vasodilator and thus permits increased blood flow in the peripheral vessels. It also decreases the viscosity of blood whose viscosity has increased as a result of the presence of increased amounts of fibrinogen. Finally, the compound helps to retard the sickling process.

As indicated earlier, the treatment is primarily useful for the management of the pain of acute sickle cell attacks. But, because of the fact that the treatment has no effect on the basic presence of hemoglobin S which is responsible for the sickling tendency, the treatment does not affect a cure of the disorder and relapses do occur. Nevertheless, the relief provided in acute crises is significant and valuable to the patient and any recurrences which may take place can be treated in the same manner as the original occurrence.

DESCRIPTION OF THE PREFERRED EMBODIMENTS

For use in the present treatment, the active compound is administered intravenously to a patient in sickle cell crisis by slow infusion of a solution in glucose serum. The rate of infusion is about 1.0 to 1.5 ml. of solution per minute. Usually, a solution is prepared using one ampule (containing 25 mg. of compound) in 25 to 50 ml. of glucose serum. In less severe situations, the compound can be given intramuscularly.

The exact dosage used would range from 25 to 200 mg./day for adults intravenously and 5 to 50 mg./day for children intravenously. The exact dosage and schedule of administration will vary depending on the amount needed to provide relief in each particular instance. Thus, for example, for adults, administration can vary from a single dose of 25 mg. to that same dose administered for several days; and higher doses can be administered in a similar manner. Also, as may be appropriate for the resolution of the pain, the administration can be repeated at 6 hr. intervals. In particularly severe situations, concomitant oral administration may also be desirable using capsules at 30 to 100 mg./day. Similar oral treatment can be used for maintenance therapy after management of the initial attack. But, such maintenance treatment provides only limited protection against recurrence and, in the event of a recurrence of an acute attack, the previously described intravenous treatment would be repeated until the attack is managed.

The following examples illustrate the practice of this invention but are not intended to limit its scope.

EXAMPLES

A group of 29 patients suffering from sickle cell anemia with varying manifestations of pain were treated with Cetiedil on occasion of 40 crises by the method described earlier. Excellent results were observed in 32 cases, good results in 4 cases and moderate results in 2 cases. There were 4 relapses and 2 failures. The failures involved children with severe chest infections.

More specifically, eight patients experiencing the pain of sickle cell crises were treated with Cetiedil using the technique for intravenous administration described earlier. Each individual had presented repeated painful sickle cell attacks, generally since childhood. The average annual number of attacks for these subjects was 6 to 8. In all the patients, an almost immediate cessation of the acute attack of pain occurred. The following additional observations were made in the treatments:

I. A 20 yr. old patient who experienced pain in the left thigh was treated with Cetiedil (one 25-mg. ampule in 25 ml. of glucose serum, intravenously, followed by 3 capsules at 30 mg./day orally). Pain was experienced during infusion but it disappeared after 2 hours. There was no relapse observed.

II. A 25 yr. old patient who experienced severe pain in the left thigh was treated with Cetiedil (one 25 mg. ampule in 25 ml. of glucose serum, intravenously). Pain was experienced following infusion but disappeared after 3 hours. No relapse was observed.

III. A 13 yr. old patient who experienced severe bone pain and thoracic-muscular pain was treated with Cetiedil (one 25 mg. ampule in 25 ml. of glucose serum, intravenously). Disappearance of pain after 5 hours but relapse at 24 hours and 36 hours. Treatment repeated. More pain fourth day.

IV. A 46 yr. old patient had been treated over a long period for osteonecrosis of the femoral head. Pain was experienced, coinciding with appearance of scapulohumeral osteonecrosis. Treated with Cetiedil (one 25 mg. ampule in 25 ml. glucose serum intravenously every two days plus calciparine plus calcium). Progressive improvement was observed with disappearance of pain after 6 days. Relapse after 3 months.

V. A 20 yr. old patient had been followed up and receiving irregular treatment for 5 years. Osteoarticular, lumbosacral, vascular pain was experienced. The general condition was deficient. Treated with Cetiedil (one 25 mg. ampule in 50 ml. glucose serum 3 days in succession followed by Cetiedil capsule at 100 mg./day). Progressive disappearance of pain in 6 days with recovery of general condition. Headache induced by maintenance therapy so dose reduced to 60 mg./day.

VI. A 25 yr. old patient experienced diffuse pain and was treated with Cetiedil (one 25 mg. ampule intravenously, then capsules at 30 mg./day). Immediate disappearance of pain but relapse on the 7th, 11th, 12th and 15th day after starting treatment. Intravenous dosage repeated as initially with disappearance of pain. No relapse after 2 months then.

VII. A 4 yr. old patient experienced osteoarticular, bone, muscle, pelvic, and lower limb pain which prevented walking. Treated with Cetiedil (12.5 mg.—½ ampule-in 25 ml. glucose serum intravenously at 6 hour intervals followed by 1 capsule at 30 mg./day). Disappearance of pain was observed during infusion but relapse 6 hours after initiation of treatment. Total and final disappearance of pain 15 hours later but relapse after 2 months.

VIII. A 4 yr. old patient experienced severe thoracic pain with appearance of acute pneumopathy and acute anemia. Treated with antibiotics and Cetiedil (12.5 mg.—½ ampule—daily intravenously for 3 days followed by 30 mg./day orally). Pain disappeared 24 hours after initiation of treatment with progressive improvement. Pneumopathic syndrome disappeared in 3 days. No relapse.

What is claimed is:

1. A method for the treatment of the acute pain crises of sickle cell anemia which comprises the administration of an effective amount of the citrate or the oxalate salt of the 2-(hexahydro-1H-azepin-1-yl)ethyl ester of α-cyclohexyl-3-thiopheneacetic acid.

2. A method according to claim 1 in which the administration is intravenous.

3. A method according to claim 1 in which the citrate salt of the 2-(hexahydro-1H-azepin-1-yl)ether ester of α-cyclohexyl-3-thiopheneacetic acid is administered intravenously.

4. A method according to claim 3 in which the citrate salt is in the form of the hydrate and is administered to adults at 25 to 200 mg./day.

* * * * *